United States Patent [19]

Inamoto et al.

[11] Patent Number: 4,887,576
[45] Date of Patent: Dec. 19, 1989

[54] METHOD OF DETERMINING ACCEPTABILITY OF AN EXHAUST CONCENTRATION SENSOR

[75] Inventors: Norio Inamoto; Takahiro Minowa, both of Wako, Japan

[73] Assignee: Honda Giken Kogyo Kabushiki Kaisha, Tokyo, Japan

[21] Appl. No.: 252,025

[22] Filed: Sep. 28, 1988

Related U.S. Application Data

[63] Continuation of Ser. No. 921,538, Oct. 21, 1986, abandoned.

[30] Foreign Application Priority Data

Oct. 21, 1985 [JP] Japan .................................. 60-234772

[51] Int. Cl.⁴ .............................................. F02D 41/26
[52] U.S. Cl. .................................... 123/479; 123/489
[58] Field of Search ................ 123/440, 479, 489; 73/23

[56] References Cited

U.S. PATENT DOCUMENTS 3,916,848  11/1975  Schmidt ............................ 123/489 X
4,121,548  10/1978  Hattori et al. .................... 123/489 X
4,177,787  12/1979  Hattori et al. .................... 123/489 X
4,434,764   3/1984  Hasegawa et al. ............... 123/489 X
4,624,232  11/1986  Saito et al. ...................... 123/440 X
4,655,892   4/1987  Satta et al. ...................... 204/424 X

FOREIGN PATENT DOCUMENTS 54-5129   1/1979  Japan .
57-137633 8/1982  Japan .

Primary Examiner—Tony M. Argenbright
Attorney, Agent, or Firm—Lyon & Lyon

[57] ABSTRACT

A valve indicative of the concentration of an emission component contained in exhaust from an internal combustion engine is outputted by an exhaust concentration sensor arranged in the exhaust system of the engine, and the value is compared with a predetermined reference value, followed by obtaining a ratio of a first time period during which the sensor output value exceeds the predetermined reference value to a second time period during which the sensor output value is less than the reference value. The acceptability of the exhaust concentration sensor is determined based on the obtained ratio. Preferably, the sensor is judged to be of acceptable quality when the ratio lies within a predetermined range and defective when the ratio lies outside the predetermined range.

2 Claims, 2 Drawing Sheets

METHOD OF DETERMINING ACCEPTABILITY OF AN EXHAUST CONCENTRATION SENSOR

This is a continuation of co-pending application Ser. No. 921,538 filed on Oct. 20, 1986, now abandoned.

BACKGROUND OF THE INVENTION

This invention relates to a method of determining the acceptability of an exhaust concentration sensor arranged in the exhaust system of an internal combustion engine for sensing the concentration of an emission component contained in the engine exhaust.

A commonly employed air-fuel ratio feedback control system for internal combustion engines is described, for example, in Japanese Provisional Patent Publication (Kokai) No. 57-137633. In accordance with this conventional system, the air-fuel ratio of the mixture supplied to an internal combustion engine is subjected to feedback control to obtain a stoichiometric mixture ratio that will maximize the conversion efficiency of a three-way catalyst arranged in the engine exhaust system in such a manner that the amount of fuel supplied to the engine is set to a basic value dependent, for example, upon the rotational speed of the engine and the absolute pressure in the engine intake pipe, the basic value being corrected by a correction value which conforms to parameters inclusive of the concentration of oxygen contained in the engine exhaust sensed by an exhaust concentration sensor (hereinafter referred to as an "$O_2$ sensor") arranged in the engine exhaust system.

The $O_2$ sensor employed in the above feedback control system uses a substance such as zirconium oxide as a sensing element. Utilizing the fact that the amount of oxygen ion which permeates the interior of the zirconium oxide varies depending upon the difference between the partial pressure of oxygen in the atmosphere and the partial pressure of oxygen contained in the exhaust gas, the $O_2$ sensor senses oxygen concentration in the exhaust gas to output a voltage which varies as a function of the above-mentioned variation in partial pressure difference.

If the $O_2$ sensor employed in the above-described air-fuel ratio feedback control system should happen to be defective, the air-fuel ratio of the mixture supplied to the engine will indicate an abnormal value and, as a result, appropriate control of the engine will not be possible.

Accordingly, methods of determining whether the $O_2$ sensor is faulty have been proposed. Basically, these conventional methods are of two types. One method proposed by Japanese Provisional Patent Publication (Kokai) No. 54-5129 judges the $O_2$ sensor to be faulty when the value of its output voltage departs from a range defined by the maximum and minimum values that the sensor can exhibit when operating normally. The other method proposed by U.S. Pat. No. 3,916,848 relies upon the so-called "changeover" of the $O_2$ sensor, in which the sensor output voltage level changes from the rich side to the lean side, or vice versa, with respect to a predetermined reference value. According to this method, the $O_2$ sensor is judged to be defective when the changeover fails to occur within a predetermined period of time.

With the former method, the $O_2$ sensor will not be judged to be abnormal even if it possesses an output characteristic in which the sensor output voltage is offset to the rich or lean side, so long as the output voltage level of the sensor lies within the range defined by the maximum and minimum values. Using an $O_2$ sensor having such a characteristic will cause the air-fuel ratio of the mixture to shift toward the lean or rich side. Similarly, the latter method will not find the $O_2$ sensor to be faulty even if it has the above-mentioned output characteristic favoring the rich or lean side, so long as the changeover of the $O_2$ sensor output occurs within the predetermined time period.

Conventionally, it is general practice to install an $O_2$ sensor, which has been found acceptable through one of the aforementioned methods, in the engine exhaust system on an automotive vehicle mass-production line and then actually run the completed vehicle to measure the amount of toxic components in the exhaust gas by the so-called "10 mode test method". Often an engine using an $O_2$ sensor judged to be acceptable in the manner set forth above will, based on the results of the test, fail to satisfy the prescribed limit values on HC or NOx emissions contained in the engine exhaust gas. When such is the case, the $O_2$ sensor must be dismounted from the vehicle and replaced. This requires considerable time and labor.

SUMMARY OF THE INVENTION

It is therefore an object of the invention to provide a method of determining the acceptability of an exhaust concentration sensor correctly without a diagnostic error.

According to the invention, the foregoing object is attained by providing a method of determining the acceptability of an exhaust concentration sensor arranged in an exhaust system of an internal combustion engine for sensing the concentration of a component contained in exhaust emitted by the engine, the method comprising the steps of comparing a sensed value outputted by the exhaust concentration sensor indicative of the concentration of the component, with a predetermined reference value, obtaining a ratio of a first time period during which the sensed value is higher than the predetermined reference value to a second time period during which the sensed value is lower than the predetermined reference value, and determining whether the exhaust concentration sensor is acceptable or not based on the obtained ratio between the first time period and the second time period.

Thus, by comparing the sensed value with the predetermined reference value, finding the ratio of the first time period to the second time period and passing judgment on the acceptability of the sensor based on this ratio, the drawbacks of the aforementioned conventional methods are eliminated to make possible an accurate determination of the sensor characteristics without committing a diagnostic error. Consequently, following its installation in a completed vehicle, the sensor almost never needs to be replaced by reason of having been found to be defective after such installation. The result in a major savings in time and labor.

The above and other objects, features and advantages of the invention will be apparent from the following description taken in conjunction with the accompanying drawings.

DETAILED DESCRIPTION

A preferred embodiment of a method of determining the acceptability of a O₂ sensor according to the invention will now be described with reference to the drawings.

Figure 1:
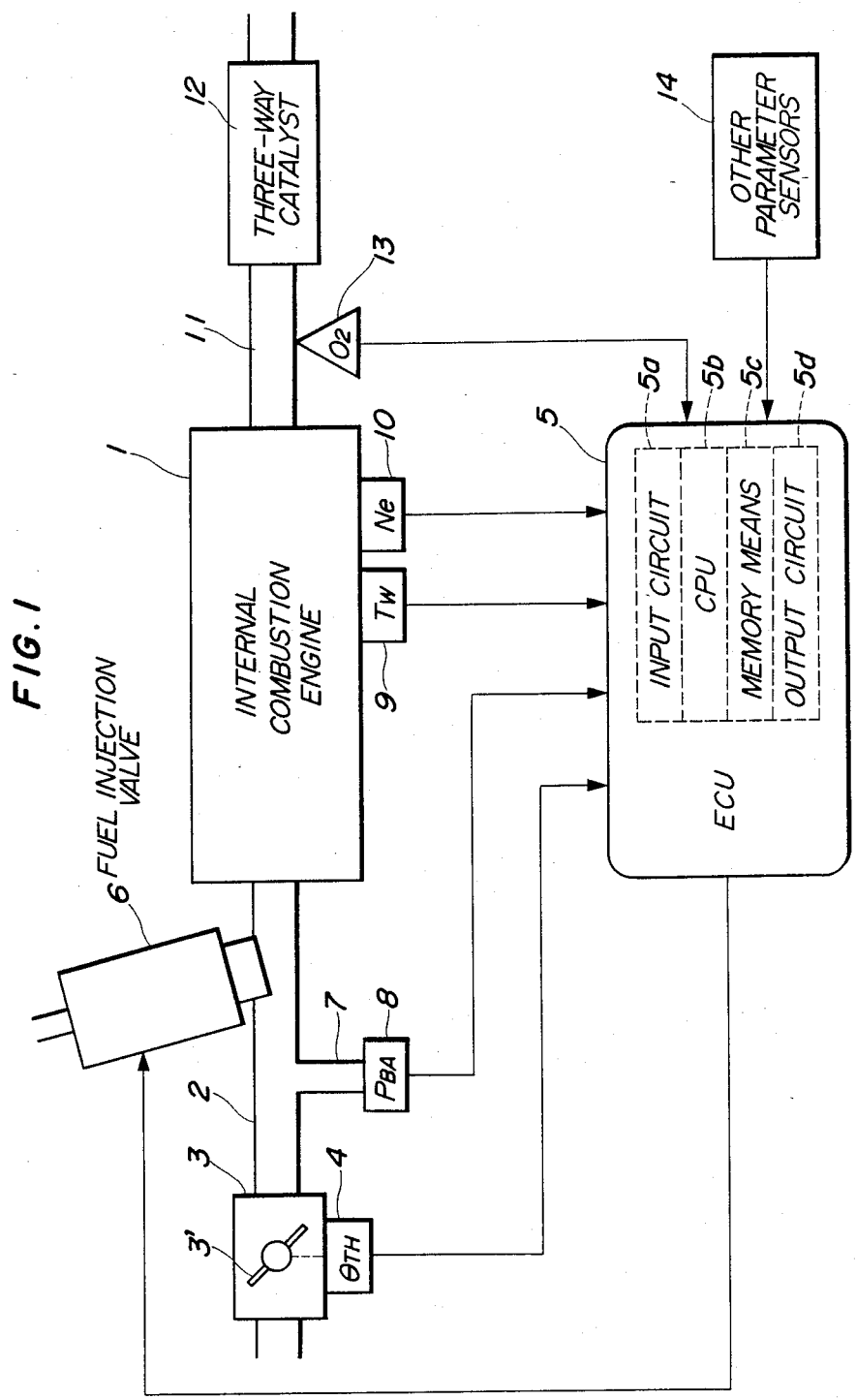
FIG. 1 is a block diagram illustrating the overall construction of a fuel supply control system representing one exemplary use of an $O_2$ sensor.

FIG. 1 illustrates the construction of one example of a system using an O₂ sensor for controlling the supply of fuel to an internal combustion engine. The internal combustion engine, designated by numeral 1, is e.g. of the four-cylinder type and has an intake pipe 2 connected thereto. The intake pipe 2 is provided therein with a throttle body 3 housing a throttle valve 3'. A throttle valve opening ($\theta$TH) sensor 4 is connected to the throttle valve 3' for converting the sensed opening of the throttle valve 3' into an electric signal, which is delivered from the sensor to an electronic control unit (hereinafter referred to as the "ECU") 5.

A fuel injection valve 6 for each one of the engine cylinders is provided in the intake pipe 2 between the engine 1 and the throttle body 3 at a location slighly upstream of the intake valve (not shown) of each cylinder. The fuel injection valve 6 is connected to a fuel pump, not shown, and is electrically connected to the ECU 5. The valve opening period of the fuel injection valve 6 is controlled by a signal from the ECU 5.

An absolute pressure (PBA) sensor 8 is connected via a pipe 7 to the intake pipe 2 at a point downstream of the throttle valve 3' of throttle body 3. An electric signal indicative of absolute pressure in the intake pipe 2 downstream of the throttle valve 3 is produced by the absolute pressure sensor 8 and delivered to the ECU 5.

The engine 1 has an engine coolant temperature sensor (hereinafter referred to as the "Tw sensor") 9 provided on its cylinder block. The Tw sensor 9, which comprises such a component as a thermistor, is mounted in the peripheral wall of a cylinder filled with engine coolant and supplies the ECU 5 with an electric signal indicative of the sensed coolant temperature. An engine rotational speed sensor (hereinafter referred to as the "Ne sensor") 10 is mounted in facing relation to the engine camshaft or crankshaft, not shown. The Ne sensor 10 outputs a crank angle signal (hereinafter referred to as the "TDC signal") at a predetermined crank angle whenever the engine crankshaft rotates through 180°, namely at a predetermined crank angle before top dead center (TDC) at the start of the suction stroke of each cylinder. The TDC signal is delivered to the ECU 5.

The engine 1 has an exhaust pipe 11 in which a three-way catalyst 12 is arranged for purifying the engine exhaust gas components of HC, CO and NOx. Inserted in the exhaust pipe 11 upstream of the three-way catalyst 12 is an O₂ sensor 13 for sensing the concentration of oxygen in the exhaust gas and providing the ECU 5 with a signal indicative of the oxygen concentration sensed.

Also connected to the ECU 5 are other parameter sensors 14 such as an atmospheric pressure sensor. These parameter sensors 14 supply the ECU 5 with their output signals representing the respective parameter values sensed.

The ECU 5 comprises an input circuit 5a which functions to shape the input signal waveforms from the various sensors, correct the voltage levels of these signals to predetermined levels and convert the values of these analog signals into digital signal values, a central processing circuit (hereinafter referred to as the "CPU") 5b, memory means 5c for storing various control programs executed by the CPU 5b as well as the results of calculations executed by the CPU 5b, and an output circuit 5d for supplying the fuel injection valve 6 with a driving signal.

Whenever the TDC signal is applied thereto, the CPU 5b calculates a fuel injection time period Tout of the fuel injection valve 6 by using the following equation, based on engine parameter signals outputted by the various sensors and delivered to the CPU 5b via the input circuit 5a:

$$\text{Tout} = Ti \times K_{O_2} \times K_1 + K_2 \quad (1)$$

where Ti represents a basic fuel injection time period of the fuel injection valve 6. The basic fuel injection time period Ti is read out of the memory means 5c on the basis of e.g. the absolute pressure PBA in the intake pipe and the engine rotational speed Ne. Further, $K_{O_2}$ is an O₂ feedback correction coefficient, described below. $K_1$ and $K_2$ represent correction coefficients and correction variables, respectively, calculated in dependence upon various engine parameter signals. $K_1$ and $K_2$ are set to requisite values dependent upon operating conditions of the engine in order to optimize operating characteristics of the engine such as driveability, exhaust emission characteristics and fuel consumption.

The aforementioned O₂ feedback correction coefficient $K_{O_2}$ has its value set in accordance with the output of the O₂ sensor 13 in FIG. 1 in an air-fuel ratio feedback control region of the engine 1 and is multiplied by the basic injection time period Ti to correct the latter. That is, the injection time period Tout and, hence, the air-fuel ratio of the mixture supplied to the engine 1, is controlled by the use of the correction coefficient $K_{O_2}$ to obtain a stoichiometric mixture ratio (e.g. 14.7) that will maximize the conversion efficient of the three-way catalyst 12, while the engine is operating in the air-fuel ratio feedback control region. More specifically, the CPU 5b compares the output value (voltage value) of the O₂ sensor 13, which output value is indicative of the oxygen concentration, and a predetermined reference value (e.g. 0.6 V). When the output value changes from the rich side to the lean side, or vice versa, with respect to the predetermined reference value, the CPU 5b executes proportional control (P-term control) for varying the correction coefficient $K_{O_2}$ by a first correction value Pi each time the change occurs. The CPU 5b executes integral control (I-term control) for varying the correction coefficient $K_{O_2}$ by a second correction value Δk whenever a predetermined period of time elapses, e.g. whenever a predetermined number of pulses of the TDC signal are generated, as long as the output value of the O₂ sensor remains on the lean side or on the rich side with respect to the predetermined reference value.

Figure 2:
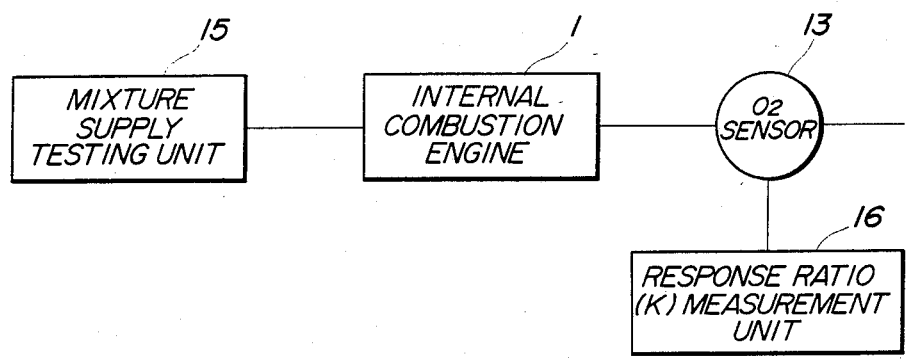
FIG. 2 is a block diagram illustrating a testing arrangement for practicing the method of the present invention.
Figure 3:
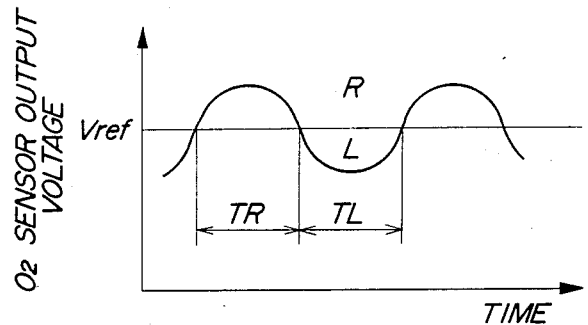
FIG. 3 is a graph illustrating a change in the output voltage of the O₂ sensor with time.

FIG. 2 is a block diagram of a response ratio (K) measuring arrangement for practicing the sensor acceptability determining method of the invention with regard to the O₂ sensor used in the fuel supply control system of an internal combustion engine, as set forth above. The $O_2$ sensor 13 submitted to measurement is mounted in the exhaust system of the internal combustion engine 1 to which the sensor is applied. The arrangement of FIG. 2 includes a mixture supply testing unit 15 adapted to prepare a mixture having a predetermined air-fuel ratio (e.g. a stoichiometric mixture ratio of 14.7) and supply the mixture to the engine 1. Connected to the output side of the $O_2$ sensor 13 is a response ratio (K) measuring unit 16 for measuring the response ratio K of the $O_2$ sensor 13. As shown in FIG. 3, the response ratio K is represented by $TR/(TR+TL)$, which is the ratio of a first time period TR during which the output voltage of the $O_2$ sensor 13 is on the rich side at a value higher than the predetermined reference value Vref (e.g. 0.6 V) to a second time period TL during which the output voltage of the $O_2$ sensor 13 is on the lean side at a value lower than the predetermined reference value Vref. The $O_2$ sensor 13 is judged to be of acceptable quality if the response ratio $K[=TR/(TR+TL)]$ lies within a predetermined requisite range (e.g. 0.5–0.6); a value of K outside this range indicates that the sensor 13 is defective. In actual practice, the mixture supply testing unit 15 operates continuously for about 10 seconds per measurement to supply the engine 1 with the mixture at the predetermined air-fuel ratio. If the $O_2$ sensor 13 is operating normally, then its output will change from the rich side to the lean side and in the reverse direction about 10 times in response to the supply of the mixture. Therefore, an average value of the response ratios $K[=TR/(TR+TL)]$ obtained for e.g. 10 changeovers in the $O_2$ sensor output is calculated and the acceptability of the $O_2$ sensor is determined based on the average value.

It is common knowledge that the amount of CO and HC emissions contained in the exhaust gas is high when the mixture is rich, whereas the amount of NOx emitted is high when the mixture is lean. Therefore, the upper and lower limit values of the predetermined range requisite for the response ratio K to determine the acceptability of the O2 sensor are set as follows: The lower limit value is set to a value $K_1$ [(a) in FIG. 4], which corresponds to a stipulated target value (maximum allowable value) (g/km) of the amount of carbon monoxide CO and hydrocarbon HC contained in the exhaust gas, decided by exhaust gas emissio regulations, and the upper limit value is set to a value $K_2$ [(b) in FIG. 4], which corresponds to a stipulated target value (maximum allowable value) (g/km) of the amount of nitrogen oxides NOx contained in the exhaust gas, decided by the regulations. Accordingly, if use is made of an $O_2$ sensor of which the response ratio K falls below the lower limit value $K_1$, the amount of CO and HC emitted will increase and exceed the stipulated target value at the shaded region A in (a) of FIG. 4 owing to the above-described feedback control operation, even though the stoichiometric ratio mixture is supplied to the engine 1. Similarly, if an $O_2$ sensor is used of which the response ratio K rises above the upper limit value $K_2$, then the amount of NOx emitted will increase and exceed the stipulated target value at the shaded region B in (b) of FIG. 4. Therefore, when the response ratio K lies within the range $K_1$–$K_2$ that satisfies all of the stipulated target values for CO, HC and NOx, the $O_2$ sensor is of acceptable quality.

Figure 4:
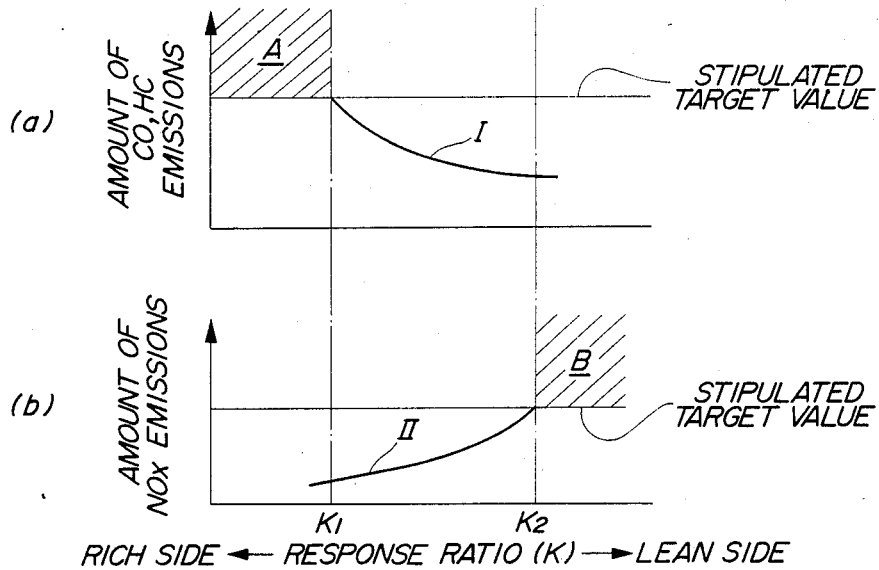
FIGS. 4(a) and 4(b) are graphs each illustrating the relationship between the amount of component emissions in exhaust gas and a response ratio K.

It should be noted that the curves I, II in (a) and (b) of FIG. 4 indicate changes in the amount of CO and HC emitted and in the amount of NOx emitted, respectively, with a change in the value of K.

As many apparently widely different embodiments of the present invention can be made without departing from the spirit and scope thereof, it is to be understood that the invention is not limited to the specific embodiments thereof except as defined in the appended claims.

What is claimed is:

1. A method of determining the acceptability of an exhaust concentration sensor arranged in an exhaust system of an internal combustion engine for sensing the concentration of a component contained in exhaust emitted by the engine, the method comprising the steps of:
    (1) continuously supplying an air-fuel mixture to the engine at a predetermined constant air-fuel ratio corresponding to a stoichiometric mixture ratio;
    (2) comparing a sensed value outputted by the exhaust concentration sensor indicative of the concentration of said component, with a predetermined reference value;
    (3) obtaining a ratio of a first time period during which the sensed value is higher than said predetermined reference value to a second time period during which said sensed value is lower than said predetermined reference value; and
    (4) determining that the exhaust concentration sensor is acceptable when the obtained ratio between the first time period and the second time period is within a predetermined range, and determining that the exhaust concentration sensor is not acceptable when the obtained ratio between the first time period and the second time period is not within the predetermined range,
    wherein said exhaust concentration sensor is arranged upstream of a three-way catalyst disposed in said exhaust system, and wherein said predetermined range of said ratio is defined by two extreme limit values, one of which is set to a maximum allowable value of the amount of carbon monoxide and hydrocarbon contained in the exhaust and the other to a maximum allowable value of the amount of nitrogen oxides contained in the exhaust.

2. A method as claimed in claim 1, including the step of supplying an air-fuel mixture having a predetermined air-fuel ratio to said engine for a predetermined period of time sufficient for said sensed value outputted by said exhaust concentration sensor to change across said predetermined reference value a plurality of times within said predetermined period of time, and wherein in said step (3) values of said ratio are obtained for said plurality of times of changing of said sensed values across said predetermined reference value, and an average value of said values of said ratio is calculated, and said step (4) is executed based on the calculated average value.

* * * * *